(12) United States Patent
Budiman

(10) Patent No.: US 11,087,868 B2
(45) Date of Patent: Aug. 10, 2021

(54) METHODS, DEVICES AND SYSTEMS FOR ANALYTE MONITORING MANAGEMENT

(71) Applicant: Abbott Diabetes Care Inc., Alameda, CA (US)

(72) Inventor: Erwin S. Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 475 days.

(21) Appl. No.: 13/629,240

(22) Filed: Sep. 27, 2012

(65) Prior Publication Data
US 2013/0085679 A1  Apr. 4, 2013

Related U.S. Application Data

(60) Provisional application No. 61/540,410, filed on Sep. 28, 2011.

(51) Int. Cl.
*A61B 5/145* (2006.01)
*G16H 20/17* (2018.01)
(Continued)

(52) U.S. Cl.
CPC ......... *G16H 20/17* (2018.01); *A61B 5/14532* (2013.01); *A61B 5/725* (2013.01);
(Continued)

(58) Field of Classification Search
CPC ... A61B 5/145; A61B 5/14503; A61B 5/1455; A61B 5/1459; A61B 5/1486;
(Continued)

(56) References Cited

U.S. PATENT DOCUMENTS

| 4,545,382 A | 10/1985 | Higgins et al. |
| 4,711,245 A | 12/1987 | Higgins et al. |

(Continued)

OTHER PUBLICATIONS

Lillacci et al. "Parameter Estimation and Model Selection in Computational Biology." PLoS Comput Biol. Mar. 5, 2010;6(3):e1000696.*
(Continued)

*Primary Examiner* — Meredith Weare
(74) *Attorney, Agent, or Firm* — Vorys, Sater, Seymour and Pease LLP

(57) ABSTRACT

Methods of analyte monitoring management are provided. The methods include indicating on a user interface a plurality of analyte management procedures available for user-selection, where the plurality of analyte management procedures relate to analyte management parameters. Embodiments include receiving an indication to initiate a first procedure of the plurality of analyte management procedures, where the first procedure is for determining a first analyte management parameter. The methods may further include outputting user-instructions associated with the first procedure; receiving analyte measurement data for the first procedure; estimating the first analyte management parameter based on the analyte measurement data; calculating a degree of certainty for the estimation of the first analyte management parameter; and, initiating an action in response to an event associated with a status of the estimation of the first analyte management parameter or the degree of certainty. Analyte monitoring devices and systems implementing the methods are also provided.

25 Claims, 9 Drawing Sheets

(51) Int. Cl.
*G16B 99/00* (2019.01)
*G16H 10/40* (2018.01)
*A61B 5/00* (2006.01)
*G16H 80/00* (2018.01)

(52) U.S. Cl.
CPC .............. *G16B 99/00* (2019.02); *G16H 10/40* (2018.01); *G16H 80/00* (2018.01)

(58) Field of Classification Search
CPC ... A61B 5/157; A61B 5/1451; A61B 5/14532; A61B 5/1468; A61B 5/1477; A61B 5/14546; A61B 5/1473–14735; A61B 5/14865; A61M 2230/201; G06F 19/34–36; G01N 2800/042; G16B 99/00; G16H 20/17
See application file for complete search history.

(56) References Cited

U.S. PATENT DOCUMENTS

| | | | |
|---|---|---|---|
| 5,262,035 A | 11/1993 | Gregg et al. | |
| 5,262,305 A | 11/1993 | Heller et al. | |
| 5,264,104 A | 11/1993 | Gregg et al. | |
| 5,320,725 A | 6/1994 | Gregg et al. | |
| 5,356,786 A | 10/1994 | Heller et al. | |
| 5,509,410 A | 4/1996 | Hill et al. | |
| 5,593,852 A | 1/1997 | Heller et al. | |
| 5,601,435 A | 2/1997 | Quy | |
| 5,628,890 A | 5/1997 | Carter et al. | |
| 5,820,551 A | 10/1998 | Hill et al. | |
| 5,822,715 A | 10/1998 | Worthington et al. | |
| 5,899,855 A | 5/1999 | Brown | |
| 5,918,603 A | 7/1999 | Brown | |
| 6,071,391 A | 6/2000 | Gotoh et al. | |
| 6,121,009 A | 9/2000 | Heller et al. | |
| 6,134,461 A | 10/2000 | Say et al. | |
| 6,144,837 A | 11/2000 | Quy | |
| 6,161,095 A | 12/2000 | Brown | |
| 6,175,752 B1 | 1/2001 | Say et al. | |
| 6,270,455 B1 | 8/2001 | Brown | |
| 6,284,478 B1 | 9/2001 | Heller et al. | |
| 6,377,894 B1 | 4/2002 | Deweese et al. | |
| 6,503,381 B1 | 1/2003 | Gotoh et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,560,471 B1 | 5/2003 | Heller et al. | |
| 6,579,690 B1 | 6/2003 | Bonnecaze et al. | |
| 6,600,997 B2 | 7/2003 | Deweese et al. | |
| 6,605,200 B1 | 8/2003 | Mao et al. | |
| 6,605,201 B1 | 8/2003 | Mao et al. | |
| 6,654,625 B1 | 11/2003 | Say et al. | |
| 6,676,816 B2 | 1/2004 | Mao et al. | |
| 6,730,200 B1 | 5/2004 | Stewart et al. | |
| 6,736,957 B1 | 5/2004 | Forrow et al. | |
| 6,746,582 B2 | 6/2004 | Heller et al. | |
| 6,764,581 B1 | 7/2004 | Forrow et al. | |
| 6,881,551 B2 | 4/2005 | Heller et al. | |
| 6,893,545 B2 | 5/2005 | Gotoh et al. | |
| 6,932,894 B2 | 8/2005 | Mao et al. | |
| 7,090,756 B2 | 8/2006 | Mao et al. | |
| 7,167,818 B2 | 1/2007 | Brown | |
| 7,299,082 B2 | 11/2007 | Feldman et al. | |
| 7,389,133 B1* | 6/2008 | Kotulla .............. | A61B 5/14503 600/309 |
| 7,811,231 B2 | 10/2010 | Jin et al. | |
| 7,822,557 B2 | 10/2010 | Chen et al. | |
| 2002/0019747 A1* | 2/2002 | Ware .................... | G06F 19/345 705/2 |
| 2007/0095661 A1 | 5/2007 | Wang et al. | |
| 2008/0177164 A1 | 7/2008 | Heller et al. | |
| 2008/0179187 A1 | 7/2008 | Ouyang et al. | |
| 2009/0006061 A1 | 1/2009 | Thukral et al. | |
| 2010/0198034 A1 | 8/2010 | Thomas et al. | |
| 2010/0212675 A1* | 8/2010 | Walling .............. | G06F 19/3406 128/898 |
| 2010/0213057 A1 | 8/2010 | Feldman et al. | |
| 2010/0218132 A1* | 8/2010 | Soni et al. ..................... | 715/771 |
| 2010/0298685 A1 | 11/2010 | Hayter et al. | |
| 2010/0324392 A1 | 12/2010 | Yee et al. | |
| 2010/0326842 A1 | 12/2010 | Mazza et al. | |
| 2011/0015511 A1* | 1/2011 | Bousamra et al. ........... | 600/365 |
| 2011/0098548 A1* | 4/2011 | Budiman ............. | G06F 19/3456 600/365 |
| 2011/0120865 A1 | 5/2011 | Bommakanti et al. | |
| 2011/0124993 A1 | 5/2011 | Bommakanti et al. | |
| 2011/0124994 A1 | 5/2011 | Bommakanti et al. | |
| 2011/0124996 A1* | 5/2011 | Reinke .............. | A61M 5/14248 600/365 |
| 2011/0126188 A1 | 5/2011 | Bernstein et al. | |
| 2011/0178820 A1* | 7/2011 | Soni .................... | A61B 5/0002 705/3 |
| 2011/0184267 A1* | 7/2011 | Duke ................. | A61B 5/14532 600/365 |
| 2011/0213225 A1 | 9/2011 | Bernstein et al. | |
| 2011/0224523 A1 | 9/2011 | Budiman | |
| 2011/0256024 A1 | 10/2011 | Cole et al. | |
| 2011/0257495 A1 | 10/2011 | Hoss et al. | |
| 2012/0157801 A1 | 6/2012 | Hoss et al. | |

OTHER PUBLICATIONS

Fukui et al. "Serum prostate-specific antigen levels in men with type 2 diabetes." Diabetes Care. May 2008;31(5):930-1. (Year: 2008).*
Nakajima et al. "Low serum amylase in association with metabolic syndrome and diabetes: A community-based study." Cardiovasc Diabetol. Apr. 17, 2011;10:34. (Year: 2011).*
EP Extended Search Report received in corresponding EP application No. 18172728, dated Jul. 30, 2018.

\* cited by examiner

| EVENT | ACTION | | |
|---|---|---|---|
| ① Degree of certainty below threshold and baseline time not expired: | A - continue estimation of parameter with more data | | |
| | B - indicate estimated remaining time until completion relative to predetermined baseline time | | |
| ② Degree of certainty below threshold and baseline time expired: | C - discontinue estimation / defer till later | | |
| | D - continue estimation beyond baseline time | | |
| ③ Degree of certainty above threshold: | E - complete procedure | | |
| | F - provide recommendation: | 1 - medication dosage (e.g., bolus dosage, etc.) | |
| | | 2 - determine currently unavailable procedures and indicate currently available procedures | |
| | G - provide status of procedures: | 3 - indicate completed and/or incompleted procedures | |
| | | 4 - indicate confidence level score(s) of completed procedure and/or levels of completeness | |
| ④ Event compromises estimation or degree of certainty: | H - discontinue procedure: | 5 - defer till later time | |
| | | 6 - indicate status of the incomplete procedure | |
| | | 7 - recommend when the failed procedure is currently available again | |

FIG. 2

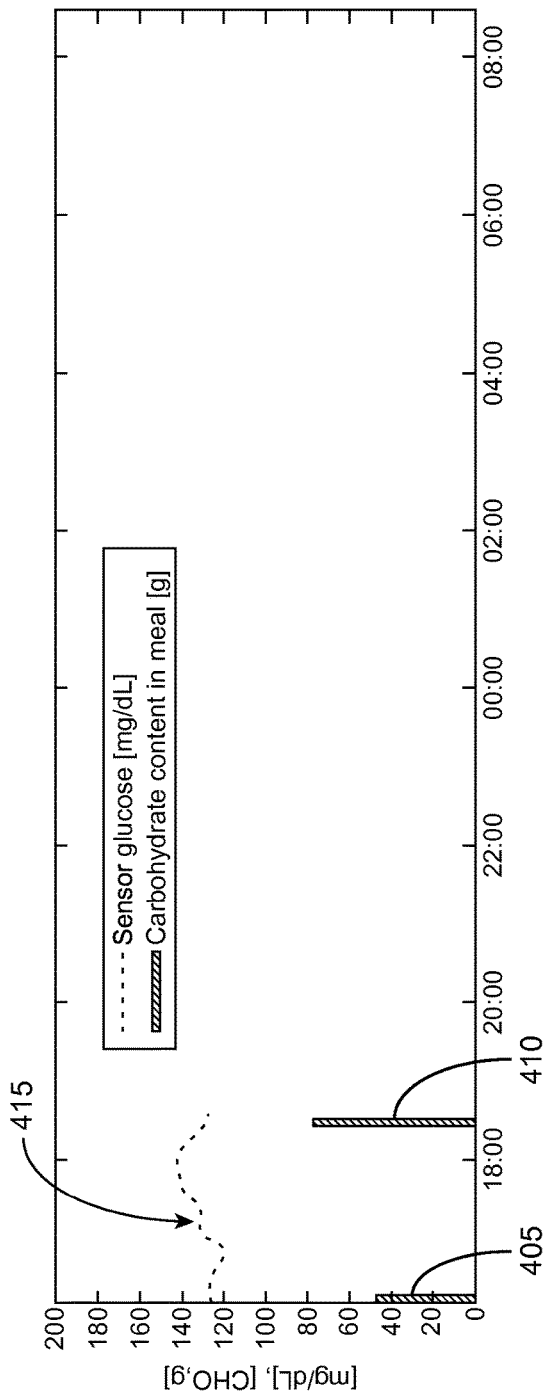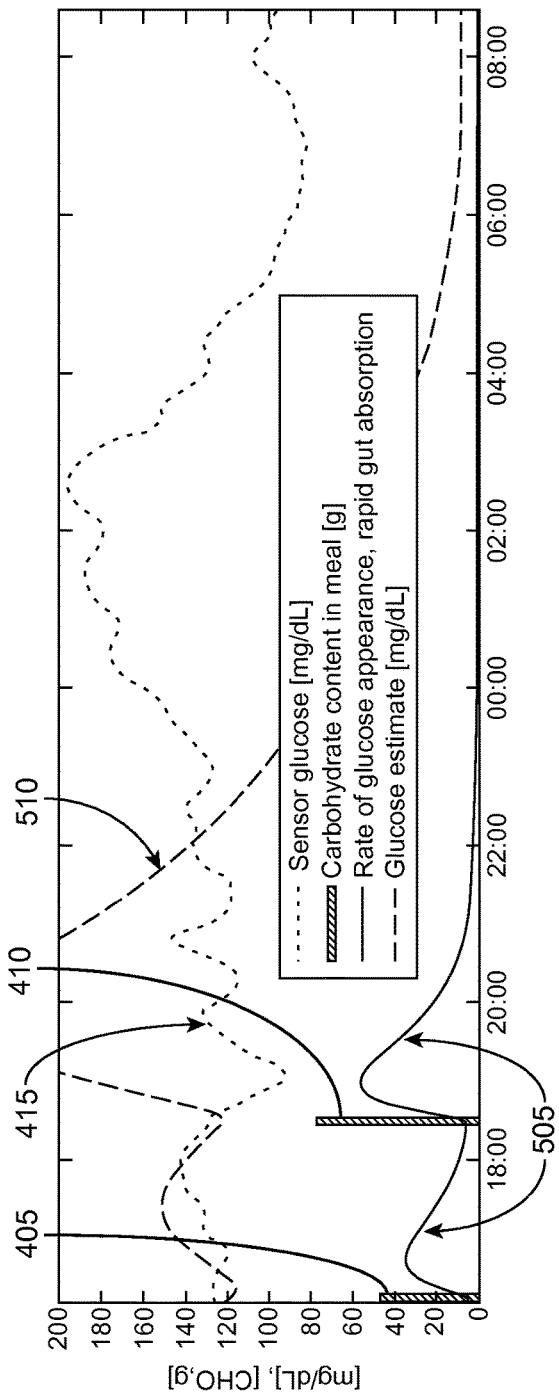

METHODS, DEVICES AND SYSTEMS FOR ANALYTE MONITORING MANAGEMENT

CROSS-REFERENCE TO RELATED APPLICATIONS

This application claims priority based to U.S. Provisional Application No. 61/540,410, filed Sep. 28, 2011, the disclosure of which is incorporated by reference herein in its entirety.

INTRODUCTION

Diabetes patients regularly consult with their health care practitioner (HCP) in order to assess the progress of their diabetes management, and to evaluate areas in need for improvement. This includes keeping diligent record of relevant information such as meal times and amount, insulin intake, exercise, and glucose measurements. Minimizing the inconvenience imposed on the patients is important in many aspects, the least of which is the likelihood that a less inconvenient regimen has a better chance of overall compliance, which in turn maximizes the utility of the information provided to the HCP in the follow-up visit.

Accordingly, devices and methods that increase user convenience are desired. The subject invention meets this need.

SUMMARY

Methods of analyte monitoring management are provided. The methods include indicating on a user interface a plurality of analyte management procedures available for user-selection, where the plurality of analyte management procedures relate to analyte management parameters. Embodiments include receiving an indication to initiate a first procedure of the plurality of analyte management procedures, where the first procedure is for determining a first analyte management parameter. The methods may further include outputting user-instructions associated with the first procedure; receiving analyte measurement data for the first procedure; estimating the first analyte management parameter based on the analyte measurement data; calculating a degree of certainty for the estimation of the first analyte management parameter; and, initiating an action in response to an event associated with a status of the estimation of the first analyte management parameter or the degree of certainty. Analyte monitoring devices and systems implementing the methods are also provided.

INCORPORATION BY REFERENCE

Additional embodiments of analyte monitoring systems suitable for practicing methods of the present disclosure are described in U.S. Pat. Nos. 6,175,752, 6,134,461, 6,579,690, 6,605,200, 6,605,201, 6,654,625, 6,746,582, 6,932,894, 7,090,756, 5,356,786; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,377,894; 6,600,997; 6,514,460; 5,628,890; 5,820,551; 6,736,957; 4,545,382; 4,711,245; 5,509,410; 6,540,891; 6,730,200; 6,764,581; 6,503,381; 6,676,816; 6,893,545; 6,514,718; 5,262,305; 5,593,852; 6,746,582; 6,284,478; 7,299,082; 7,811,231; 7,822,557; U.S. Patent Application Publication Nos. 2010/0198034; U.S. Patent Application Publication No. 2010/0324392; U.S. Patent Application Publication No. 2010/0326842 U.S. Patent Application Publication No. 2007/0095661; U.S. Patent Application Publication No. 2008/0179187; U.S. Patent Application Publication No. 2008/0177164; U.S. Patent Application Publication No. 2011/0120865; U.S. Patent Application Publication No. 2011/0124994; U.S. Patent Application Publication No. 2011/0124993; U.S. Patent Application Publication No. 2010/0213057; U.S. Patent Application Publication No. 2011/0213225; U.S. Patent Application Publication No. 2011/0126188; U.S. Patent Application Publication No. 2011/0256024; U.S. Patent Application Publication No. 2011/0257495; U.S. Patent Application Publication No. 2010/0213057; and U.S. Patent Application Publication No. 2012/0157801, the disclosures of each of which are incorporated herein by reference in their entirety.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

FIG. 2 illustrates a chart with examples of events and corresponding actions in response to the events, according to one embodiment.

FIG. 4 illustrates a chart of a patient's glucose, meal, and insulin during one sample day, according to one embodiment.

FIG. 5 illustrates a chart of an estimate of the rate of glucose appearance due to a relatively rapidly absorbed meal, according to one embodiment.

DETAILED DESCRIPTION

Figure 1:
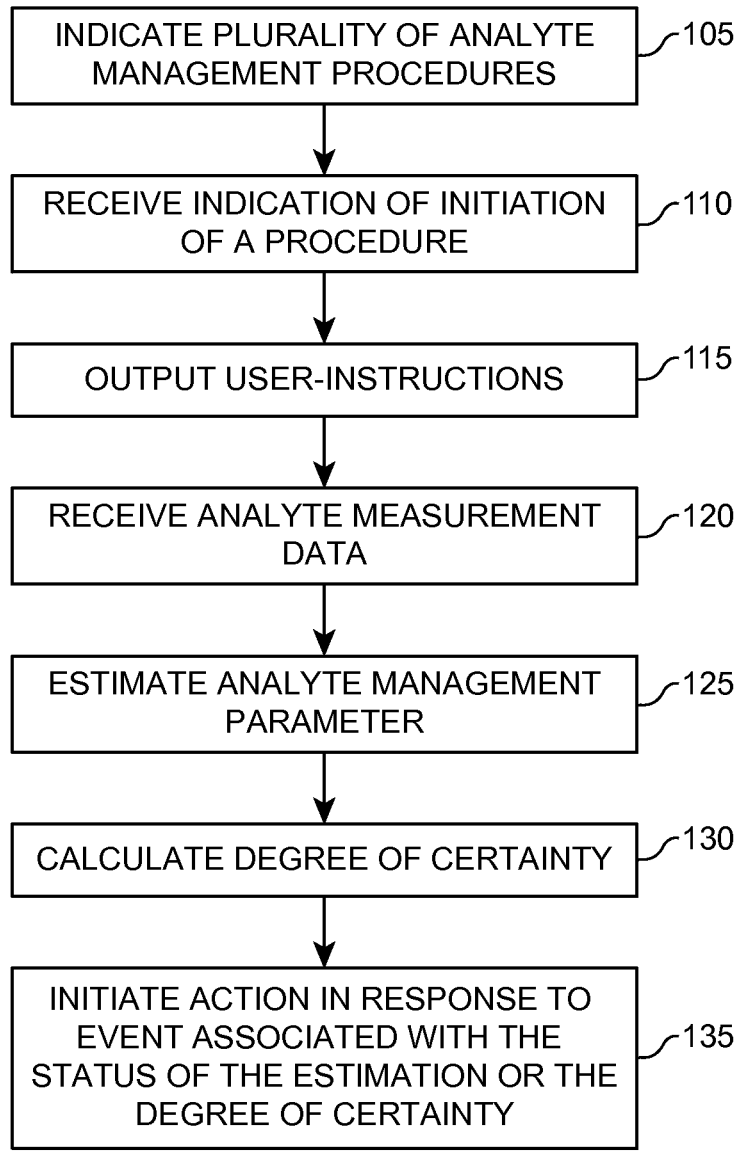
FIG. 1 illustrates a flowchart for a method for analyte monitoring management, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

As summarized above, in some aspects of the present disclosure, methods of analyte monitoring management are provided. The methods include indicating a plurality of analyte management procedures available for user-selection, where the plurality of analyte management procedures is for determining analyte management parameters. The methods include receiving an indication to initiate a first procedure of the plurality of analyte management procedures, where the first procedure is for determining a first analyte management parameter. The methods further include outputting user-instructions associated with the first procedure; receiving analyte measurement data for the first procedure; estimating the first analyte management parameter based on the analyte measurement data; calculating a degree of certainty for the estimation of the first analyte management parameter; and, initiating an action in response to an event associated with a status of the estimation of the first analyte management parameter or the degree of certainty.

Furthermore, as summarized above, in some aspects of the present disclosure, analyte monitoring devices are provided. The analyte monitoring devices include a processor and memory operably coupled to the processor. The memory includes instructions stored therein. The instructions include instructions for indicating a plurality of analyte management procedures available for user-selection, where the plurality of analyte management procedures is for determining analyte management parameters. The instructions include instructions for receiving an indication to initiate a first procedure of the plurality of analyte management procedures, where the first procedure is for determining a first analyte management parameter. The instructions further include instructions for outputting user-instructions associated with the first procedure; instructions for receiving analyte measurement data for the first procedure; instructions for estimating the first analyte management parameter based on the analyte measurement data; instructions for calculating a degree of certainty for the estimation of the first analyte management parameter; and, instructions for initiating an action in response to an event associated with a status of the estimation of the first analyte management parameter or the degree of certainty.

Still further, as summarized above, in some aspects of the present disclosure, analyte monitoring systems are provided. The analyte monitoring systems include an analyte sensor and an analyte monitoring device receiving analyte measurement data from the analyte sensor. The analyte monitoring device including a processor and memory operably coupled to the processor. The memory includes instructions stored therein. The instructions include instructions for indicating a plurality of analyte management procedures available for user-selection, where the plurality of analyte management procedures is for determining analyte management parameters. The instructions include instructions for receiving an indication to initiate a first procedure of the plurality of analyte management procedures, where the first procedure is for determining a first analyte management parameter. The instructions further include instructions for outputting user-instructions associated with the first procedure; instructions for receiving analyte measurement data for the first procedure; instructions for estimating the first analyte management parameter based on the analyte measurement data; instructions for calculating a degree of certainty for the estimation of the first analyte management parameter; and, instructions for initiating an action in response to an event associated with a status of the estimation of the first analyte management parameter or the degree of certainty.

For example, in some aspects of the present disclosure, real-time, progressive assistance to the patient in achieving a set of pre-determined procedures outlined by a HCP is provided, alleviating inconveniences associated with the procedures. The user and/or the HCP may be able to view certain information about the extent of useful information gained during the procedures in order to provide positive feedback to the user going through the procedure, and in order to provide degree of certainty context to the HCP so that the amount of treatment titration can be adjusted accordingly.

Depending on the particular analyte management parameter to be determined by a given procedure, one or more tasks may be required or asked of the patient in order to successfully determine the parameter. For instance, for glucose monitoring management, examples tasks include fasting to determine basal dose, taking or avoiding specific meals, potentially delaying meal boluses, etc. Various analyte management parameters may be useful in to infer certain characteristics of the patient, or to directly refine the rules for their diabetes management. Examples may include total daily dose, bolus to basal ratio, carb ratio, insulin sensitivity factor, target glucose, etc.

For example, with regard to glucose monitoring management, delaying a meal bolus allows the HCP to infer the patient's carb ratio, e.g., how the patient's glucose increases given a particular composition and amount of meal taken. For instance, the HCP may ask that the patient keep sufficiently frequent glucose record after a meal is consumed, and wait for a predetermined amount of time before taking a meal and correction bolus, so that the device is able track the progress of the patient's glucose using frequent glucose data from the CGM system, and determine whether the patient's carb ratio has been adequately determined. If the level of confidence (e.g., degree of certainty) achieves a certain threshold before the predetermined time as estimated by the HCP, then the CGM system can alert the user that they no longer need to wait in administering a meal &/correction bolus, and even provide a means to calculate the proper amount. If the degree of certainty has not reached a certain threshold, but the user already announced the administration of insulin for whatever reason, then the CGM system can discontinue the procedure and remind the user that they may still need to repeat the procedure again at another time.

For example, the device may be preprogrammed with the specific procedures and threshold values provided by the HCP, and will allow the patient to advance from one procedure to another in a predetermined sequence, or to choose which procedures to complete first if a choice is available. This empowers the patient and makes the set of procedures less rigid and more flexible from the patient's perspective.

FIG. 1 illustrates a flowchart for a method for analyte monitoring management, according to one embodiment. At block 105, a plurality of analyte management procedures are indicated to the user of the analyte monitoring device. The procedures determine analyte management parameters. For example, the plurality of analyte management procedures may be indicated in a list that is displayed on a display of an analyte monitoring device. The plurality may be displayed in any variety of formats—e.g., as a list, as a pull-down menu, as individual icons, etc. It should be appreciated that the plurality of analyte management procedures may be indicated in other manners in other embodiments—e.g., audibly.

The plurality of analyte management procedures may be, for example, a list of procedures needed by a HCP to titrate a patient's diabetes treatment. In one embodiment, the analyte monitoring device may be programmable, for example, to enable the HCP to program the analyte monitoring device with the plurality of procedure, or to modify a previously programmed plurality. The analyte monitoring device may receive, for example, the programming input and store the corresponding plurality of analyte management procedures in memory.

In one embodiment, a list of procedures needed by a HCP to titrate a patient's diabetes treatment may be provided to the analyte monitoring device, and the HCP able to enter and/or modify the list of applicable procedures, or setting in each available procedure. For instance, the HCP assigns a subset, or all, of the available procedures for the patient to perform before their next visit. Procedures that require a particular sequence of completion may be treated as a series of steps, and procedures that are independent may appear as multiple items in the patient's checklist, for instance. In another embodiment, the list of procedures may be varied to cover a more advanced level of treatment. For example, the initial list of procedures may be aimed to determine a single basal rate, a single correction factor, and a single insulin sensitivity factor. Once the parameters associated with these properties are well known after following the procedures over time, the HCP may choose a different list that allows for a split basal rate, with differing AM and PM amounts. Correction factors and insulin sensitivity factors may also be varied over differing meal times such as AM vs. PM, breakfast vs. lunch vs. dinner, snacks, etc.

The programming of the device may be performed in a variety of ways. For example, the device may include user input (e.g., buttons, touchscreen, etc.) that enable the HCP to program the device. In other instances, the analyte monitoring device may be able to receive the programming input from a remote device, such as a computer at the HCP, via wired or wireless communication. It should be appreciated that the analyte monitoring device may also access the internet to receive programming input.

At block 110, an indication of an initiation of one of the procedures is received. The initiated procedure is used to determine an analyte management parameter. The user may, for example, select one of the plurality displayed on the screen to initiate one of the procedures. The analyte monitoring device may include, for example, user input elements (e.g., buttons, touchscreen, etc.) that enable the user to initiate the procedure. It should be appreciated that in some embodiments, the user may select more than one procedure to initiate. In some instances, the analyte monitoring device may simultaneously initiate the procedure, and in other instances, the device may perform the procedures sequentially.

At block 115, user-instructions are output. For example, user-instructions for the selected procedure may be provided on the display of the device. The user-instructions assist the patient to guide the patient. In some instances, the user-instructions may be provided via other methods than text, such as by audible instructions, visual instructions such as graphical illustrations and/or videos. Some procedures may require very little user-instruction. In some instances, the user-instructions include a confirmation to begin the procedure. In some instances the user-instructions include an indication that the procedure has been initiated and is being performed—e.g., a symbol or light (e.g., LED) that indicates the procedure has begun—thus instructing the user to proceed with the procedure.

At block 120, analyte measurement data for the selected procedure is received. The analyte measurement data is used in the determination of the analyte management parameter. The analyte measurement data may, for example, be originally derived from a transcutaneously implanted sensor that communicates the analyte measurement data to the analyte monitoring device. In one embodiment, the implanted sensor is implanted in interstitial fluid and provides analyte measurement data continuously to the analyte monitoring device (e.g., such as in continuous glucose monitoring (CGM)

systems). In another embodiment, the implanted sensor may provide analyte measurement data intermittently or periodically.

At block 125, the analyte monitoring device estimates the analyte management parameter associated with the selected procedure. The analyte management parameter may be any parameter that is useful in analyte management. For example, for glucose management, example parameters may include carb-ratio, insulin sensitivity factor, bolus to basal ratio, target glucose, etc. It should be appreciated that these analyte management parameters are exemplary and that other parameters may be applicable. Furthermore, it should be appreciated that the analyte monitoring device may implement any variety of algorithms to derive the analyte management parameters. The algorithms may include various input factors such as the analyte measurement data, and/or other relevant data that may assist in the parameter estimation. For example, for glucose management, relevant data may relate to food intake, food composition (e.g., carbohydrate, fat, and protein composition), exercise duration and intensity, medication intake or dosage amount, etc.

At block 130, a degree of certainty is calculated for the estimate. The degree of certainty may be continuously calculated as more data (e.g., analyte measurement data) is obtained, or it may be performed intermittently or periodically at various times (e.g., every 10 seconds, 30 seconds, 1 minute, 10 minutes, etc.). It should be appreciated that many different algorithms of varying complexity may be used to perform such a function. In one embodiment, a threshold degree of certainty may be used to represent a sufficient certainty that the parameter estimation is accurate. Such a threshold may be predetermined and may vary from parameter to parameter. For example, when the parameter estimation is cast in the form of an Extended Kalman Filter, the best estimate and variance of the parameter is updated at every calculation sample instance (e.g., every 10 seconds, 30 seconds, 1 minute, 10 minutes, etc.). Additional information about an Extended Kalman Filter is described in Applied Optimal Estimation written by Arthur Gelb. (Gelb, Arthur; Applied Optimal Estimation; Cambridge, Mass.; MIT Press; 1974), the entirety of which is incorporated herein by reference.

At block 135, an action is initiated in response to an event associated with a status of the estimation of the first analyte management parameter or the degree of certainty. In some embodiments. For example, when the degree of certainty exceeds the threshold, the parameter estimation may be considered accurate, or sufficiently accurate, and the procedure completed. In some embodiments, additional actions are taken in addition to completing the procedure. For example, a status of the plurality of procedures may be provided after the completion of the procedure. A status screen may indicate, for example, whether each of the procedures is completed or incomplete. If the Extended Kalman Filter framework is used, when the variance is small enough to remain below a predetermined threshold, then the degree of certainty of that parameter estimate is deemed to be sufficient.

In one embodiment, a confidence level score is provided for completed procedures. The confidence level score provides the user with an indication as to the degree of the certainty for the estimation. In this way, if the user chooses to, they can repeat the procedure again in hopes to improve the results of the procedure. In some embodiments, more than one level of completeness may exist for a procedure. For example, in one embodiment, three levels of completeness may exist, representing an incomplete level, reasonably complete level, and a best completion level. Other numbers of levels may also be implemented in other embodiments. Such levels of completeness may, in some instances, psychologically encourage the user to review completed and incomplete procedures and try to make them all as complete as possible. The various levels of completeness may be indicated in any variety of manners—e.g., color-coded (e.g., red for incomplete, yellow for reasonably complete, and green for best completion), graphics, symbols (e.g. zero to three stars), characters, numbering or ranking system, etc.

It should be appreciated that specific statuses may be provided—e.g., for completed procedures only, for incomplete procedures only, or for combinations or subsets thereof. In some instances, only the complete procedures with low confidence level scores or levels of completeness may be displayed.

In one embodiment, the remaining procedures of the plurality may be provided for the user to enable the user to select another procedure. All of the procedures and their statuses may be displayed, for example. In one embodiment, the analyte monitoring device recommends procedures from the plurality for the user to select. For example, incomplete procedures may be recommended since they have not been performed yet. Other procedures, such as completed procedures with low confidence level scores and/or levels of completeness may also be recommended to provide better results.

In one embodiment, the analyte monitoring device may determine which remaining procedures are currently available to be performed. For example, some procedures may not be available due to factors that make the procedure difficult or impossible to run successfully. For example, some parameter determinations may require fasting or an absence of medication intake (e.g., insulin intake). In such case, when food or medicine has recently been taken, those procedures may be classified as currently unavailable, and thus not recommended to the user. On the other hand, some parameters may be capable of being determined based on the factors or circumstances at the completion of a given procedure. In such case, those parameters are determined to be currently available and are thus recommended to the user. Recommendations may encourage the user to perform more procedures and further assist the user to keep track of which procedures to do, and which are currently available or unavailable to run.

In one embodiment, a therapeutic recommendation or instruction may be provided upon completion of a procedure. For example, a medication dosage may be calculated and recommended to the user. An insulin dosage may be recommended, for example, to bring a user's glucose level back into the target range. In some instances, the insulin dosage calculation may be based on the estimated parameter from the completed procedure, such as a carb-ratio parameter.

In one instance, an event may occur that compromises the estimation of the analyte management parameter or the degree of certainty of the estimation of the analyte management parameter. For example, a procedure such as for carb-ratio determination may require specific circumstances, such as fasting or absence of medication intake for the duration of the procedure. If, for example, food or medicine is taken within such time, the estimation of the parameter and the degree of certainty is compromised.

In response to such an event, the analyte monitoring device may discontinue the procedure to prevent compromised results and/or to prevent wasting the user's time performing a test if such test is likely compromised. In some instances, the procedure may be temporarily discontinued or deferred to another time. For example, the analyte monitoring device may wait to a future time to recommend the procedure to the user—e.g., after a predetermined period of time, or when such procedure becomes currently available again. The additional actions (e.g., status, recommendation, etc.) for completed procedures described above may also be applicable here as well. For example, statuses and recommendations may also be provided to the user after the procedure has been discontinued.

In one embodiment, a procedure has a predetermined baseline period of time associated with the procedure. The baseline period of time may be a standard or default period of time that is used to determine the associated analyte management parameter. For example, the HCP may require the analyte measurement data collected for the baseline period of time, such as 3 hours, 6 hours, etc., to determine an associated analyte management parameter. However, the analyte monitoring device may estimate the parameter within the threshold degree of certainty before the duration of the baseline period of time. In such case, the continuation of the procedure for the baseline period of time may be an unnecessary inconvenience that the user does not have to endure. In some embodiments, in response to the degree of certainty exceeding the threshold before the baseline period of time, the analyte monitoring device completes the procedure. Additional actions, such as status, recommendations, etc., may also be performed here as well.

In one embodiment, an estimated time remaining may be indicated for the procedure. In this way, the user may be provided with an estimate of the time remaining to complete the procedure. The user may find this information useful to determine whether to continue the procedure—e.g., if constraints of the procedure are unbearable or undesirable (e.g., fasting or absence of medication). The estimated time remaining may also encourage the user to continue a procedure. For instances, if the estimated time remaining is short in comparison to the overall duration of time for the procedure, the user may not wish to have to restart and perform the entire procedure, but rather continue for the shorter remainder of the procedure.

The estimated time remaining may be calculated, for example, based on the elapsed time since the start of the procedure and the progression of the degree of certainty over time. For instance, the time estimation can be a simple calculation based on elapsed time given estimated completion, and then assuming the same rate of completion, calculate the corresponding time for the remainder percentage. For example, if it took 3 hours so far for an estimated 75% completion of the task, then the remainder 25% should take around 1 hour, and since 1 hour is significantly shorter than 3, displaying this may encourage the user (e.g., patient) to complete the task rather than abandon it in lieu of other activities they need to do.

In one embodiment, the estimated time remaining is indicated after decreasing below a threshold period of time—e.g., a predetermined period of time (e.g., 10 minutes, 30 minutes, 1 hour, etc.), or a predetermined period of time relative to the baseline period of time (e.g., a percentage of time such as 10%, 20%, 50%, etc.).

In some aspects of the present disclosure, the analyte monitoring device transmits information gathered for the plurality of procedures and transmits it to a remote device. The information gathered may include analyte measurement data acquired by the device and/or results acquired from performing the procedures (e.g., the determination of analyte management parameters, statuses, recommendations, etc.). The remote device may be any data processing device capable of receiving transmitted data—e.g., a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), etc. The information gathered during one or more procedures may be transmitted to a remote device via wired or wireless communication. For example, the HCP may upload the information at the user's next visit using a personal computer or handheld device. Alternatively, the information gathered may be transmitted via the internet and provided to the HCP.

In some instances, at a follow-up visit, the HCP can upload all the analyte measurement data as is and perform the assessment for the user's titration without any consideration of the results of procedures performed by the analyte monitoring device. In some instances, the HCP may use the results of the procedures to inform their decision. For example, they can perform a sanity check on whether the user's insulin sensitivity factor as inferred by the HCP conforms to the value assessed by the device. In addition, procedures that yielded less than ideal confidence level scores and levels of completeness, and procedures that result in non-concordance can be discussed with the user in order to identify future areas of improvement.

In some instances, the HCP may use the results of the procedures and/or recommendations by the device to create or modify the user's treatment and plurality of procedures accordingly. The analyte monitoring device may analyze the information gathered and make recommendations based on the information gathered. For example, if certain aspects have not been satisfactorily determined by the information gathered, the device makes a suggestion on which areas of treatment can be reliably titrated, and which areas need to wait for further information. If the HCP and user agree to further titration, for example, the HCP can then set a new set of procedures from the available options in the device, and start the procedure over again as discussed above.

Accordingly, the analyte monitoring device may receive programming input to program the analyte monitoring device with a new plurality of analyte management procedures or to modify the existing plurality. The HCP may, for example, review the information gathered by the analyte monitoring device and modify the treatment, and then program the analyte monitoring device via user input on the device, via a remote device, etc.

In some aspects of the present disclosure, the plurality of analyte management procedures exists in a plurality of sets, in which successive sets allows for a more detailed and tailored determination of analyte management parameters. For example, the initial list of procedures may be aimed to determine a single basal rate, a single correction factor, and a single insulin sensitivity factor. Once the parameters associated with these properties are well known after following the procedures over time, the HCP may choose a different list that allows for a split basal rate, with differing AM and PM amounts. Correction factors and insulin sensitivity factors may also be varied over differing meal times such as AM vs. PM, breakfast vs. lunch vs. dinner, snacks, etc.

FIG. 2 illustrates a chart with examples of events and corresponding actions in response to the events, according to one embodiment. The events are associated with a status of the estimation of the first analyte management parameter or the degree of certainty. It should be appreciated that the events and actions illustrated are exemplary and that the principles of the present disclosure are not limited to only those events and actions shown. It should also be appreciated that more than one action may be taken in response to a single event.

Reference numeral 1 represents an event where a determination is made that the degree of certainty is below a threshold before the baseline time has expired. In one instance, the procedure is continued and the estimation of the analyte management parameter is continued using more analyte measurement data, as represented by reference letter A. In another instance, the estimated remaining time is indicated, as represented by reference letter B.

Reference numeral 2 represents an event where a determination is made that the degree of certainty is below a threshold and the baseline time expires. In the instance shown at reference letter C, the estimation is discontinued or deferred to a later time. In the instance shown at reference numeral D, the estimation is continued beyond the baseline time. For example, the continuation may be automatic, with or without user notification. In some instances, the device may require user approval or ask the user whether to proceed or discontinue.

Reference numeral 3 represents an event where a determination is made that the degree of certainty is above a threshold. The device completes the procedure, as represented at reference letter E. The device may further provide a recommendation and/or provide a status of the procedures, as represented at letters F and G, respectively. The recommendation may be, for example, a medication dosage as described above; a list of currently available procedures and/or currently unavailable procedures, as described above; etc. In some instances, the recommendation may be based off of the parameter that was estimated in the procedure. For example, using the parameter may be carb-ratio or insulin sensitivity factor, and then used in a calculation to determine a therapeutic recommendation (e.g., an insulin dosage amount).

The status may, for example, relate to the procedure that was just completed, or may include more than one procedure, such as a status of all completed procedures, a status of all incomplete procedures, a status of all procedures in the plurality, or any other categorization or combination of procedures. In one instance, as shown, all the procedures are indicated and their status as completed or incomplete is shown. In some embodiments, a confidence level score and/or a level of completeness may be indicated. It should be appreciated that combinations of actions may be implemented in some embodiments.

Reference numeral 4 represents an event that compromises the estimation of the analyte management parameter or the degree of certainty of the estimation. The procedure may, for example, be discontinued. In some instances, the device may defer the procedure until a later time, indicate the status of the incomplete procedure, and/or provide recommendation for how to proceed, etc. For example, the device may recommend restarting the procedure if it may be restarted and properly performed after the occurrence of the event, or it may recommend what steps need to be taken, or conditions met, to repeat the procedure. As another example, the device may recommend other procedures that are currently available for initiation despite the occurrence of the event.

Figure 3:
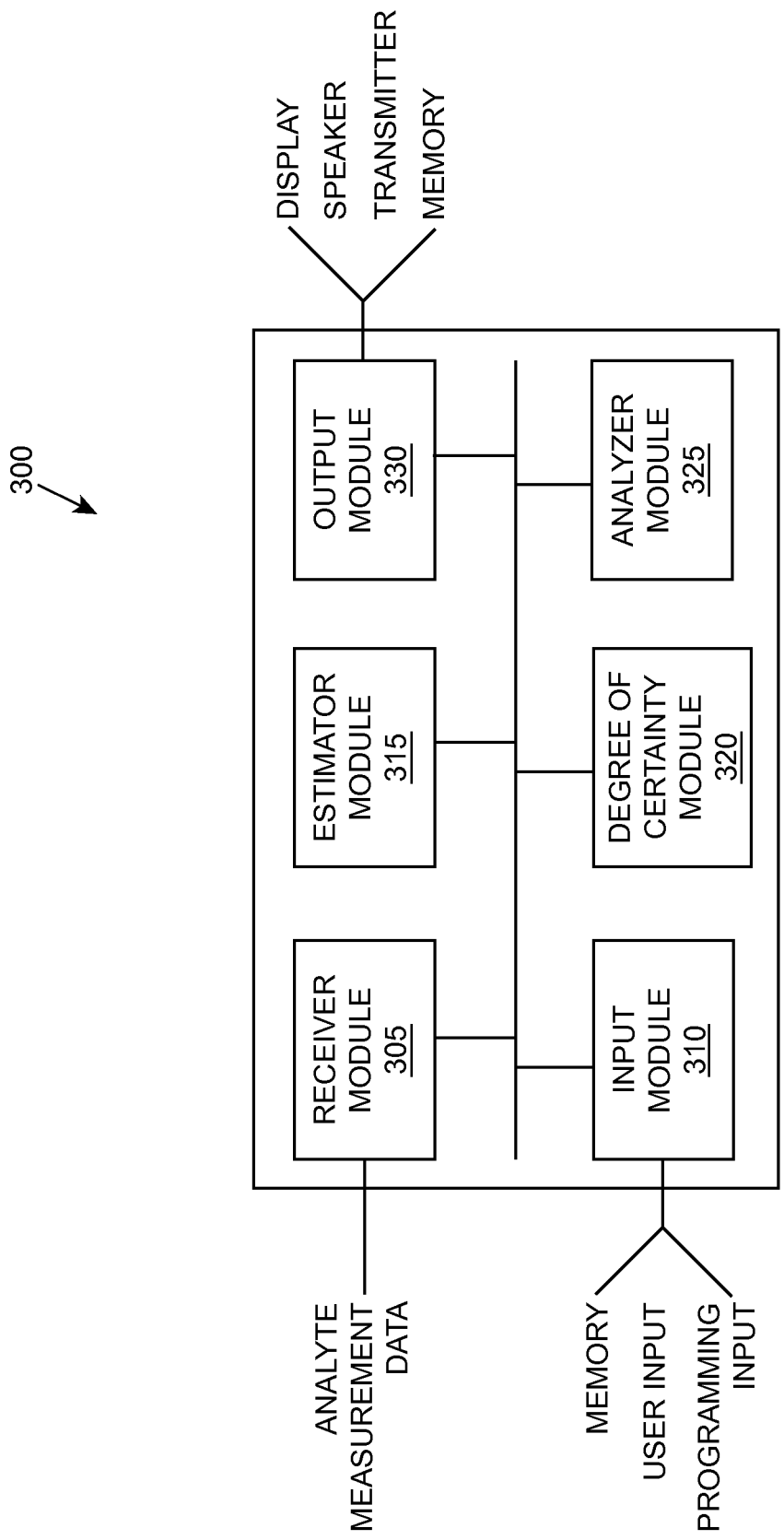
FIG. 3 illustrates a functional block diagram of components within an analyte monitoring device that perform the methods described above, according to one embodiment.

FIG. 3 illustrates a functional block diagram of components within an analyte monitoring device that perform the methods described above, according to one embodiment. In FIG. 3, device 300 includes a receiver module 305, input module 310, estimator module 315, degree of certainty module 320, analyzer module 325, and output module 330.

The receiver module 305 receives analyte measurement data. For example, the receiver module 305 may receiver analyte measurement data from an implanted sensor that wireless communicates with the receiver module 305. The receiver module 305 may receive continuous glucose measurement, for example, or alternatively receive intermittent glucose data from other glucose measurement devices. In another embodiment, the receiver module 305 may receive analyte measurement from one or more analyte monitoring devices. For instance, this may include wired and wireless transmission from another device, and/or user input into the system—e.g., after reading the measurements from one or more analyte monitoring devices.

Input module 310 receives user input. For example, the input module 310 may receive user (e.g., user) input to initiate a procedure, provide additional data (e.g., food intake, medication intake, exercise activity, etc.), or to respond to user-instructions or questions provided by the device. The input module 310 may also receive programming input by the user (e.g., HCP) to create or modify a plurality of procedures. In some instances, the user input or programming input may be stored in memory and later called for by the input module 310.

Estimator module 315 estimates the analyte management parameter of an initiated procedure, and degree of certainty module 320 calculates the degree of certainty for the estimate. The analyzer module 325 monitors for events associated with the status of the estimation of the analyte management parameter or the degree of certainty. For example, the analyzer module 325 may monitor the user input for any events that compromise the procedure being performed. The analyzer module may, for example, monitor the degree of certainty to determine when it exceeds a predetermined threshold. In some instances, the analyzer module 325 performs algorithms which are used to provide recommendations (e.g., medication dosage recommendations), statuses, confidence level scores and/or levels of completeness, etc. In some embodiments, the analyzer module 325 monitors the baseline period of time and calculates the estimated time remaining.

The output module 330 outputs information (e.g., the plurality of procedures, user-instructions, statuses, recommendations, etc.) that is provided to the user (e.g., via display, speaker, etc.). The output module 330 transmits information gathered for the procedures to a remote device, either wired or wirelessly. The output module 330 may also store information within memory of the device.

It should be appreciated that one or more modules may be combined to perform the functionalities of both modules. For example, in one embodiment, the input and output modules may be combined into a single module. For instance, an input/output module may include a medication delivery module which receives and sends drug delivery infusion amounts, rates, and/or timings to one or more drug delivery devices—e.g., via wired or wireless technology. In another embodiment, the medication delivery module may receive such medication delivery information via user input into the system.

EXAMPLE

In some aspects, methods, devices, and systems of the present disclosure perform one or more predetermined procedures to identify one or more parameters, while taking into consideration the progression of glucose over time based on glucose measurements of a continuous glucose management (CGM) system and known inputs, such as meals and insulin dosing.

For example, a real-time identification can be performed utilizing the frequent glucose information and electronic event records provided by a CGM system, such that when the parameters of interest have been sufficiently identified, the device can notify the user that the procedure is complete, or it is ready to move to the next step/procedure without requiring the user to wait until a nominal but longer time specified by the HCP. An example for the determination of carb ratio is provided below, but is extendable to other procedures with proper modifications of the model being used and parameters being identified. The example assumes other relevant parameters, such as the user's insulin sensitivity factor, is known either from an initial population based value, a rule of thumb estimate for the user, or a previously completed analyte management procedure.

FIG. 4 illustrates a chart of a user's glucose (as measured by CGM or other systems) and meal during one segment of a sample day, according to one example. A carb ratio determination example is shown from a user in the afternoon through night time. The user recorded a 45 gram carbohydrate content snack 405 after 4 pm, and a 75 gram carbohydrate content dinner 410 around 6:30 pm. CGM glucose 415 is shown for the time between the snack 405 until the meal 410.

In order to estimate a parameter such as a carb ratio, the HCP may normally ask that the user consume a meal but delay insulin administration so that they can measure the peak glucose response. However, the peak response depends on various factors such as the carbohydrate and fat content. This makes the certainty of a carb ratio estimate potentially very low. In addition, if the user were to deviate from the protocol and administer insulin, the glucose response could be dramatically altered as to render the estimate virtually useless.

FIG. 5 illustrates a chart of an estimate of the rate of glucose appearance due to a relatively rapidly absorbed meal, according to one example. Again, the user recorded a 45 gram carbohydrate content snack 405 after 4 pm, and a 75 gram carbohydrate content dinner 410 around 6:30 pm. The CGM glucose reading 415 is also shown.

The rate of glucose appearance 505 due to a relatively rapidly absorbed meal is estimated. In addition, a resulting predicted glucose value 510 is also shown. The rate of glucose appearance 505 is the mechanism that allows one to estimate the carb ratio by correlating the resulting peak glucose response 415 and the carbohydrate amount of the meal 410 recorded by the user. When a large amount of insulin is present, particularly soon after meal boluses, the identification of the carb ratio becomes almost impossible. Even when no insulin is administered soon after a meal 410, the unknown fat content as well as other factors confounds the estimation problem. In the example shown, the 45 gram snack 405 resulted in glucose increasing for less than 2 hours before glucose starts to decline, the 75 gram dinner 410 resulted in a sustained glucose increase for over 4 hours.

In some aspects, the parameters are identified in real-time, accounting for reasonable ranges of physiological parameter values until a good match between glucose 415 as recorded by the CGM device and glucose estimate 510 is achieved. The rate of glucose appearance 505 estimated assumes a rapidly absorbed meal. Since the dinner meal 410 was absorbed at a much lower rate than the snack 405, the glucose estimate 510 shows a great inconsistency following dinner 410 unless adjustments are made. Until then, the resulting carb ratio may not be reliable.

Figure 6:
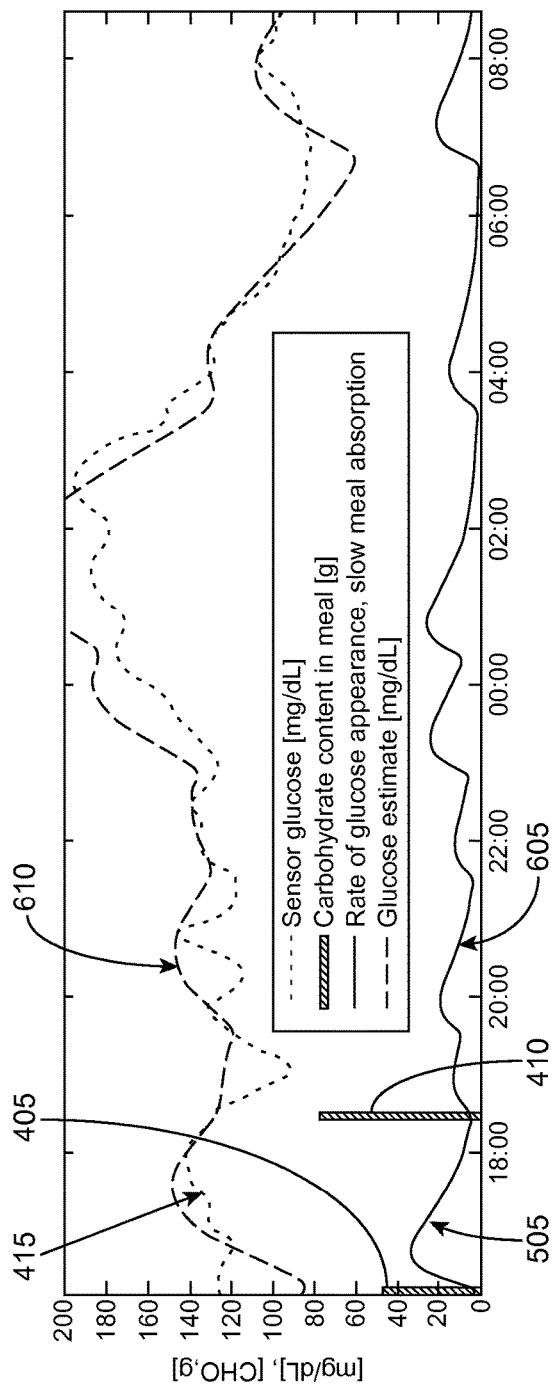
FIG. 6 illustrates a chart of an alternate estimate of the rate of glucose appearance due to a relatively slowly absorbed dinner, according to one embodiment.

FIG. 6 illustrates a chart of an alternate estimate of the rate of glucose appearance due to a relatively slowly absorbed dinner, according to one example. While the snack response 505 is unchanged from FIG. 5, the response to dinner 605 assumes a slower rate of gut absorption and glucose appearance. As shown, the glucose estimate 610 more closely matches the recorded glucose 415 by the CGM device.

Figure 7:
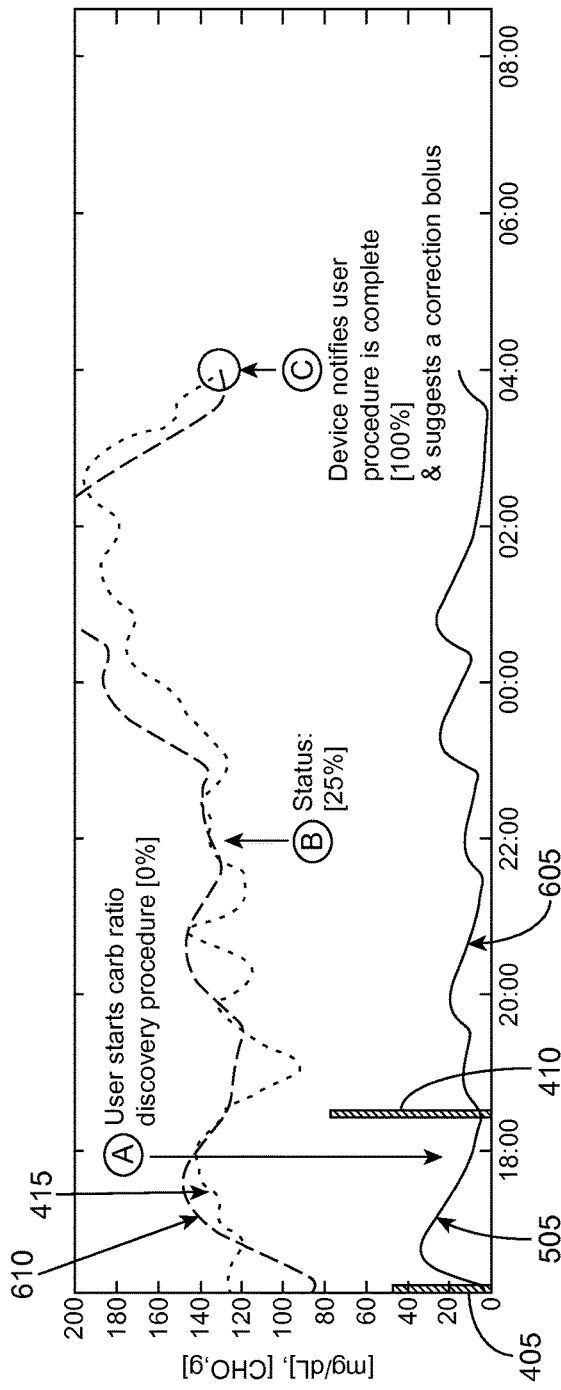
FIG. 7 illustrates a chart for a successful completion of a procedure for determining a carb-ratio, according to one embodiment.

FIG. 7 illustrates a chart for a successful completion of a procedure for determining a carb-ratio, according to one example. At reference point A, the user initiated a "carb ratio discovery" procedure (e.g., required by the HCP) sometime before 6 pm. Then, for example, per the instruction of the HCP, which may be reinforced by a reminder in the device, the user takes a 75 gram dinner 410. The parameter estimation is then performed in real-time. If the meal happens to be rapidly absorbed, then the device may have enough information within the next 2 hours as it correctly matches the peak glucose response 415 between the CGM data and the estimate 610. Then, for example, the device may notify the user that they may perform a correction bolus. If the meal happens to be slowly absorbed as shown in FIG. 7, then the device may have to wait for several more hours before the user is notified that the process is complete and that the user can now perform a correction bolus. For example, if the user checks the display of the device at around 10 pm, as represented at reference letter B, the device may indicate that the procedure is 25% complete. The user may then decide to let the procedure continue on. As shown, the user continues the procedure, and at around 4 am, the procedure is completed, as represented at reference letter C. For example, at reference letter C, the degree of certainty is calculated and determined to exceed the predetermined threshold, and thus the procedure is completed. If, for example, the user chose that a notification sound be audible if the procedure is complete, the device notifies the user at that time. In addition, in some embodiments a suggested correction bolus is then offered. The suggested amount takes into account for the projected glucose over a reasonable horizon in the future. In the absence of any known inputs such as meals, snacks, exercise, etc. taken by the user in the near future after the correction bolus, the resulting glucose data can be used to further verify whether or not the estimated carb ratio is valid. In one embodiment, the user is reminded that the next few hours can be used to complete the appropriate next analyte management procedure (e.g. insulin action time constant estimation).

Figure 8:
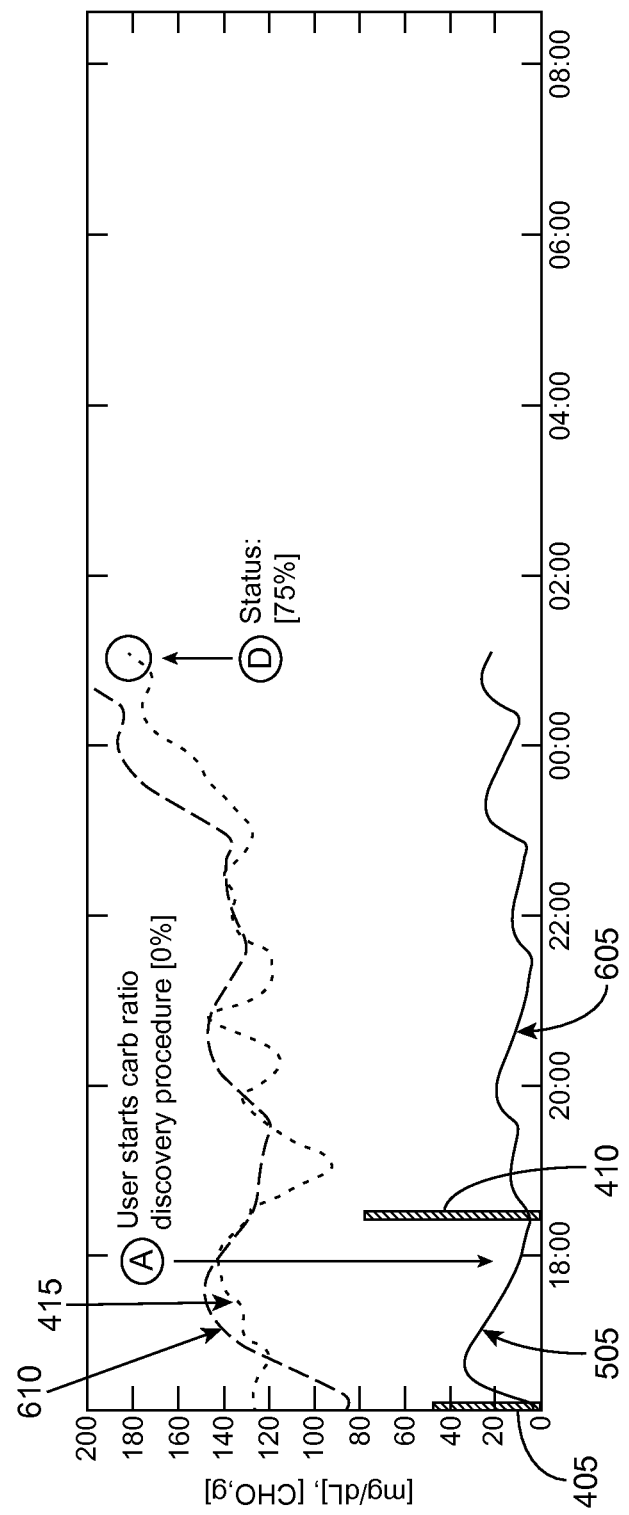
FIG. 8 illustrates a chart for a discontinuation of a procedure for determining carb-ratio, according to one embodiment.

FIG. 8 illustrates a chart for a discontinuation of a procedure for determining carb-ratio, according to one embodiment. At reference point A, the user initiated a "carb ratio discovery" procedure (e.g., required by the HCP) sometime before 6 pm. Then, the user takes a 75 gram dinner 410. The parameter estimation is then performed in real-time.

If at any point in time before proper parameter convergence, the user announces an action which compromises the estimate or degree of certainty of the estimate, then the procedure is discontinued. In some embodiments, user acknowledgement is sought before discontinuation. For example, as shown, the user checks the status of the procedure at around 1 am, as represented at reference letter D, and decides that the elevated glucose is not tolerable at this time. The user cancels the procedure and may take insulin if necessary, and may consider completing the procedure at some other time. While simply stopping the procedure compromises the confidence of the estimate since the degree of certainty had not yet exceeded the predetermined threshold, other compromising actions may have compromised the confidence of the estimation. For example, the user may have eaten more food, or taken insulin, or started an intense workout, etc. As in the previous embodiment illustrated by FIG. 7, at this point, the user might be reminded that the next few hours can be used to complete a different analyte management procedure, such as determining the time constant of insulin action.

Devices and Systems

Embodiments of the present disclosure relate to methods, devices, and systems for analyte monitoring management, such as glucose monitoring management, and are related to the detection of at least one analyte, including glucose, in body fluid. Embodiments relate to the continuous, periodic, and/or intermittent in vivo monitoring of the level of one or more analytes using a continuous, intermittent, or periodic analyte monitoring device or system. The system may include an analyte sensor at least a portion of which is to be positioned beneath a skin surface of a user for a period of time. It should also be appreciated that the present disclosure may also be applicable to discrete monitoring of one or more analytes using an in vitro blood glucose ("BG") meter and an analyte test strip.

Embodiments may include combined or combinable devices, systems and methods and/or transferring data between an in vivo continuous system and an in vivo system. In one embodiment, the systems, or at least a portion of the systems, are integrated into a single unit. For example, the analyte monitoring devices and systems may include, or communicate with, an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous, periodic, or intermittent interrogation of a level of an analyte in the user's interstitial fluid.

In one embodiment, an analyte sensor may be positioned in contact with interstitial fluid to detect the level of glucose, which detected glucose may be used to infer the glucose level in the user's bloodstream. Embodiments of the analyte sensors may be configured for monitoring the level of the analyte over a time period which may range from seconds, minutes, hours, days, weeks, to months, or longer.

In one embodiment, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more.

As demonstrated herein, the methods of the present disclosure are useful in connection with a device that is used to measure or monitor an analyte (e.g., glucose), such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof.

Figure 9:
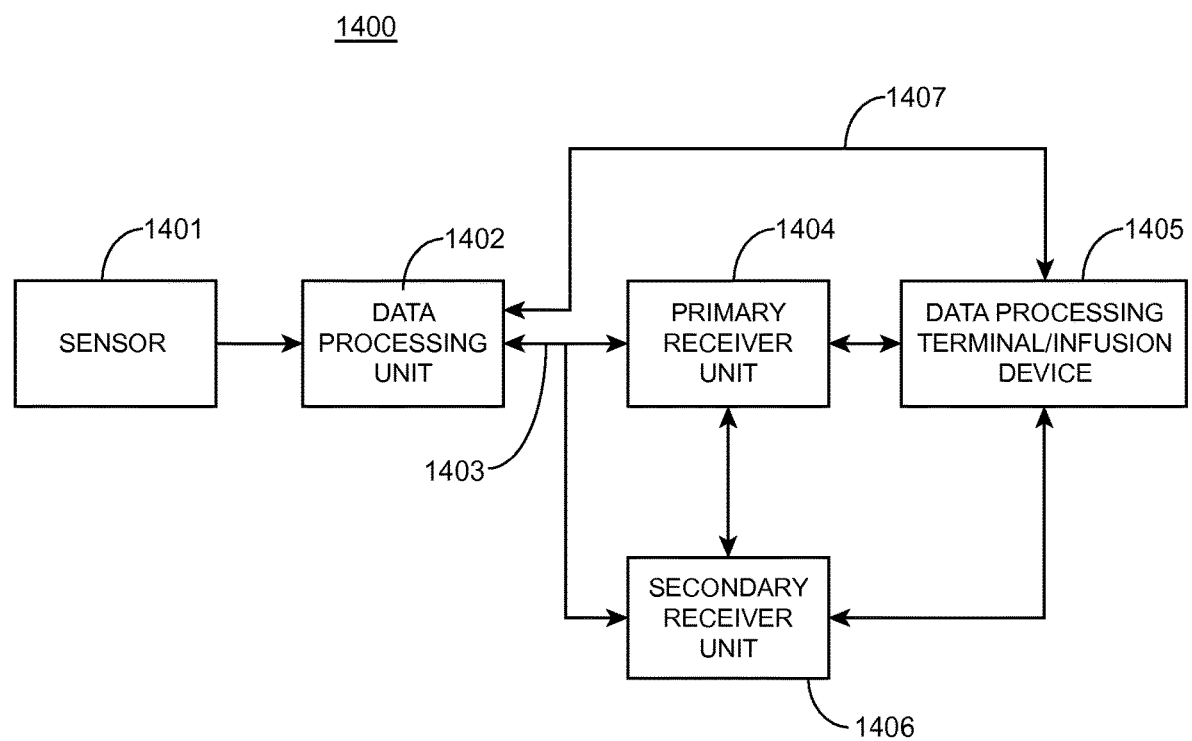
FIG. 9 illustrates an analyte monitoring system, according to one embodiment.

FIG. 9 shows an analyte (e.g., glucose) monitoring system, according to one embodiment. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 1400 includes an analyte sensor 1401, a data processing unit 1402 connectable to the sensor 1401, and a primary receiver unit 1404. In some instances, the primary receiver unit 1404 is configured to communicate with the data processing unit 1402 via a communication link 1403. In one embodiment, the primary receiver unit 1404 may be further configured to transmit data to a data processing terminal 1405 to evaluate or otherwise process or format data received by the primary receiver unit 1404. The data processing terminal 1405 may be configured to receive data directly from the data processing unit 1402 via a communication link 1407, which may optionally be configured for bi-directional communication. Further, the data processing unit 1402 may include a transmitter or a transceiver to transmit and/or receive data to and/or from the primary receiver unit 1404 and/or the data processing terminal 1405 and/or optionally a secondary receiver unit 1406.

Also shown in FIG. 9 is an optional secondary receiver unit 1406 which is operatively coupled to the communication link 1403 and configured to receive data transmitted from the data processing unit 1402. The secondary receiver unit 1406 may be configured to communicate with the primary receiver unit 1404, as well as the data processing terminal 1405. In one embodiment, the secondary receiver unit 1406 may be configured for bi-directional wireless communication with each of the primary receiver unit 1404 and the data processing terminal 1405. As discussed in further detail below, in some instances, the secondary receiver unit 1406 may be a de-featured receiver as compared to the primary receiver unit 1404, for instance, the secondary receiver unit 1406 may include a limited or minimal number of functions and features as compared with the primary receiver unit 1404. As such, the secondary receiver unit 1406 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 1404. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 1401, data processing unit 1402 and data processing terminal 1405 are shown in the embodiment of the analyte monitoring system 1400 illustrated in FIG. 9. However, it will be appreciated by one of ordinary skill in the art that the analyte monitoring system 1400 may include more than one sensor 1401 and/or more than one data processing unit 1402, and/or more than one data processing terminal 1405. Multiple sensors may be positioned in a user for analyte monitoring at the same or different times.

The analyte monitoring system 1400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 1400. For example, unique IDs, communication channels, and the like, may be used.

In one embodiment, the sensor 1401 is physically positioned in or on the body of a user whose analyte level is being monitored. The sensor 1401 may be configured to at least periodically sample the analyte level of the user and convert the sampled analyte level into a corresponding signal for transmission by the data processing unit 1402. The data processing unit 1402 is coupleable to the sensor 1401 so that both devices are positioned in or on the user's body, with at least a portion of the analyte sensor 1401 positioned transcutaneously. The data processing unit may include a fixation element, such as an adhesive or the like, to secure it to the user's body. A mount (not shown) attachable to the user and mateable with the data processing unit 1402 may be used. For example, a mount may include an adhesive surface. The data processing unit 1402 performs data processing functions, where such functions may include, but are not limited to, filtering and encoding of data signals, each of which corresponds to a sampled analyte level of the user, for transmission to the primary receiver unit 1404 via the communication link 1403. In one embodiment, the sensor 1401 or the data processing unit 1402 or a combined sensor/data processing unit may be wholly implantable under the skin surface of the user.

In one embodiment, the primary receiver unit 1404 may include an analog interface section including an RF receiver and an antenna that is configured to communicate with the data processing unit 1402 via the communication link 1403, and a data processing section for processing the received data from the data processing unit 1402 including data decoding, error detection and correction, data clock generation, data bit recovery, etc., or any combination thereof.

In operation, the primary receiver unit 1404 in one embodiment is configured to synchronize with the data processing unit 1402 to uniquely identify the data processing unit 1402, based on, for example, an identification information of the data processing unit 1402, and thereafter, to periodically receive signals transmitted from the data processing unit 1402 associated with the monitored analyte levels detected by the sensor 1401.

Referring again to FIG. 9, the data processing terminal 1405 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 1405 may further be connected to a data network (not shown) for storing, retrieving, updating, and/or analyzing data corresponding to the detected analyte level of the user.

The data processing terminal 1405 may include a drug delivery device (e.g., an infusion device) such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 1404 may be configured to integrate an infusion device therein so that the primary receiver unit 1404 is configured to administer an appropriate drug (e.g., insulin) to users, for example, for administering and modifying basal profiles, as well as for determining appropriate boluses for administration based on, among others, the detected analyte levels received from the data processing unit 1402. An infusion device may be an external device or an internal device, such as a device wholly implantable in a user.

In one embodiment, the data processing terminal 1405, which may include an infusion device, e.g., an insulin pump, may be configured to receive the analyte signals from the data processing unit 1402, and thus, incorporate the functions of the primary receiver unit 1404 including data processing for managing the user's insulin therapy and analyte monitoring. In one embodiment, the communication link 1403, as well as one or more of the other communication interfaces shown in FIG. 9, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 10:
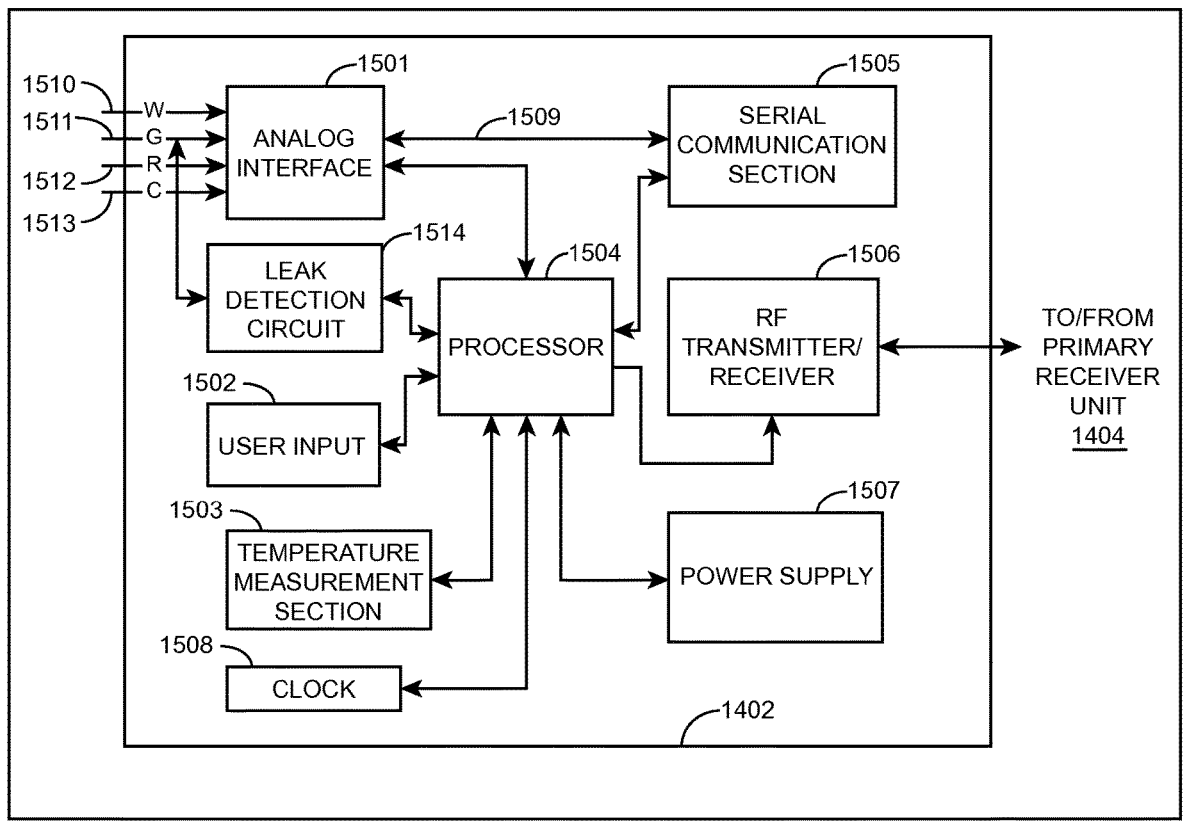
FIG. 10 illustrates a block diagram of the data processing unit shown in FIG. 9 in accordance with one embodiment.

FIG. 10 is a block diagram of the data processing unit 1402 shown in FIG. 9 in accordance with one embodiment. Data processing unit 1402 includes an analog interface 1501 configured to communicate with the sensor 1401 (FIG. 1), a user input 1502, and a temperature measurement section 1503, each of which is operatively coupled to processor 1504 such as a central processing unit (CPU). Furthermore, unit 1402 is shown to include a serial communication section 1505, clock 1508, and an RF transmitter 1506, each of which is also operatively coupled to the processor 1504. Moreover, a power supply 1507 such as a battery is also provided in unit 1402 to provide the necessary power.

It should be appreciated that in another embodiment, the data processing unit may not include all components in the exemplary embodiment shown. User input and/or interface components may be included or a data processing unit may be free of user input and/or interface components. In one embodiment, one or more application-specific integrated circuits (ASIC) may be used to implement one or more functions or routines associated with the operations of the data processing unit (and/or receiver unit) using for example one or more state machines and buffers.

As can be seen in the embodiment of FIG. 10, the analyte sensor 1401 (FIG. 1) includes four contacts, three of which are electrodes: a work electrode (W) 1510, a reference electrode (R) 1512, and a counter electrode (C) 1513, each operatively coupled to the analog interface 1501 of the data processing unit 1402. This embodiment also shows an optional guard contact (G) 1511. Fewer or greater electrodes may be employed. For example, the counter and reference electrode functions may be served by a single counter/reference electrode. In some cases, there may be more than one working electrode and/or reference electrode and/or counter electrode, etc.

Figure 11:
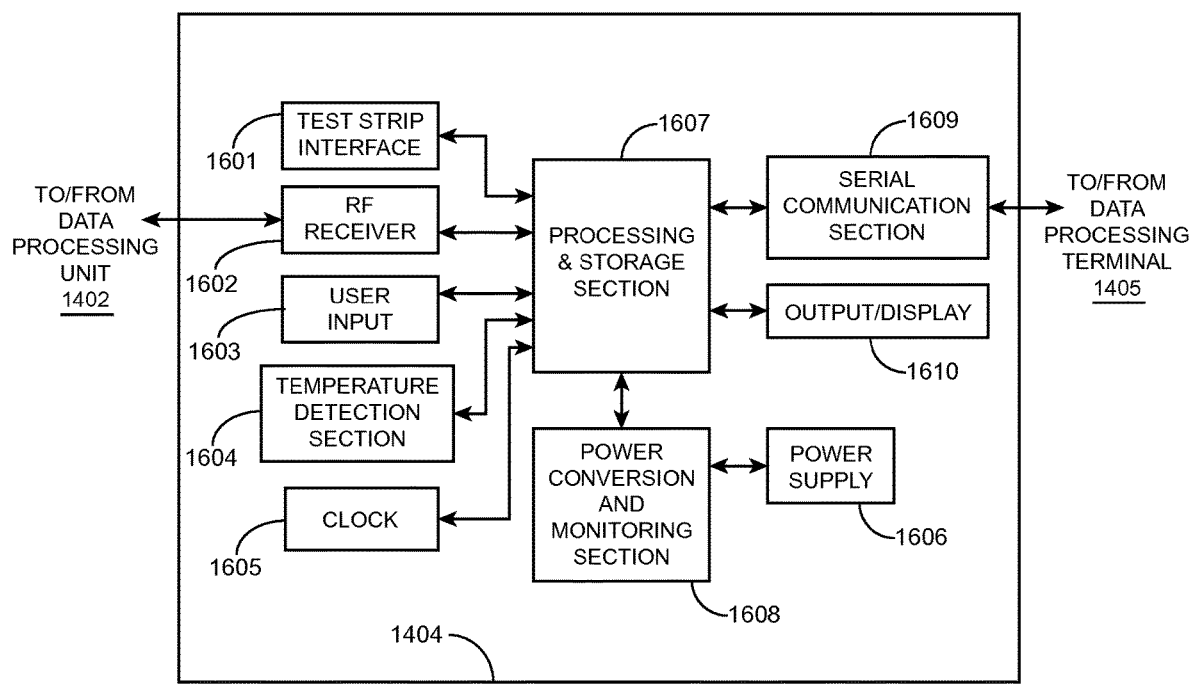
FIG. 11 illustrates a block diagram of an embodiment of a receiver/monitor unit such as the primary receiver unit of the analyte monitoring system shown in FIG. 9.

FIG. 11 is a block diagram of an embodiment of a receiver/monitor unit such as the primary receiver unit 1404 of the analyte monitoring system shown in FIG. 9. The primary receiver unit 1404 includes one or more of: a test strip interface 1601, an RF receiver 1602, a user input 1603, an optional temperature detection section 1604, and a clock 1605, each of which is operatively coupled to a processing and storage section 1607. The primary receiver unit 1404 also includes a power supply 1606 operatively coupled to a power conversion and monitoring section 1608. Further, the power conversion and monitoring section 1608 is also coupled to the processing and storage section 1607. Moreover, also shown are a receiver serial communication section 1609, and an output 1610, each operatively coupled to the processing and storage section 1607. The primary receiver unit 1404 may include user input and/or interface components or may be free of user input and/or interface components.

In one embodiment, the test strip interface 1601 includes an analyte testing portion (e.g., a glucose level testing portion) to receive a blood (or other body fluid sample) analyte test or information related thereto. For example, the test strip interface 1601 may include a test strip port to receive a test strip (e.g., a glucose test strip). The device may determine the analyte level of the test strip, and optionally display (or otherwise notice) the analyte level on the output 1610 of the primary receiver unit 1404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., FreeStyle® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 1401, confirm results of sensor 1401 to increase the confidence thereof (e.g., in instances in which information obtained by sensor 1401 is employed in therapy related decisions), etc.

In further embodiments, the data processing unit 1402 and/or the primary receiver unit 1404 and/or the secondary receiver unit 1406, and/or the data processing terminal/infusion device 1405 may be configured to receive the analyte value wirelessly over a communication link from, for example, a blood glucose meter. In further embodiments, a user manipulating or using the analyte monitoring system 1400 (FIG. 9) may manually input the analyte value using, for example, a user interface (for example, a keyboard, keypad, voice commands, and the like) incorporated in one or more of the data processing unit 1402, the primary receiver unit 1404, secondary receiver unit 1406, or the data processing terminal/infusion device 1405.

The features and techniques described in the present disclosure may be performed, for example, by the processing circuitry within the data processing unit 1402 or receiving unit 1404, or combination of both.

Additional detailed descriptions are provided in U.S. Pat. Nos. 5,262,035; 5,264,104; 5,262,305; 5,320,715; 5,593,852; 6,175,752; 6,650,471; 6,746,582, and 7,811,231, each of which is incorporated herein by reference in their entirety.

In one embodiment of the present disclosure, the analyte monitoring device includes processing circuitry that is able to determine a level of the analyte and activate an alarm system if the analyte level exceeds a threshold. The analyte monitoring device, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. patent applications, and/or non-U.S. patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

That which is claimed is:

1. A method for analyte monitoring management including using a computer having a processor for executing instructions, memory operably coupled to the processor comprising the instructions, and a display, the method comprising executing the instructions for:
    displaying for user-selection on the display a plurality of analyte management procedures for determining analyte management parameters;
    receiving an indication from a user to initiate a first procedure of the plurality of analyte management procedures for determining a first parameter of the analyte management parameters;
    displaying to the user user-instructions associated with the first procedure;
    receiving from a continuous analyte monitoring device a plurality of actual analyte measurement data of an analyte for the first procedure;
    estimating in real-time a plurality of estimated analyte measurement data for the analyte for the first procedure;
    analyzing the plurality of actual analyte measurement data and the plurality of estimated analyte measurement data in real-time, and estimating the first parameter using a Kalman Filter;
    calculating a first degree of certainty in real-time that the estimation of the first parameter is accurate, the degree of certainty being dependent on variance of the Kalman Filter, and wherein the variance of the Kalman Filter is updated upon receipt of each of the plurality of actual analyte measurement data;
    calculating and indicating an estimated time remaining for the first procedure based on an elapsed time since a start of the first procedure and a progression of the first degree of certainty in real-time over the elapsed time;
    initiating an action in response to an event, wherein the event is the first degree of certainty in real-time exceeding a predetermined threshold degree of certainty, and wherein the action comprises completing the first procedure and associating a confidence level score to the completed first procedure;
    categorizing the level of completeness of the first procedure based on the action, the level of completeness being one of:
        a reasonable level of completeness based on the confidence level score being a low confidence level score, or
        a best level of completeness based on the confidence level score being above the low confidence level score; and
    displaying to the user on the display an indication of the level of completeness.

2. The method of claim 1, wherein the first procedure comprises a first predetermined baseline of time to receive the plurality of actual analyte measurement data, the event is the first degree of certainty in real-time exceeding the predetermined threshold degree of certainty before the first predetermined baseline of time is reached, and the action is completing the first procedure before the first predetermined baseline of time is reached.

3. The method of claim 2, wherein the first procedure comprises fasting for the first predetermined baseline of time and the action further comprises an indication that the fasting can be terminated.

4. The method of claim 2, wherein the first procedure comprises eating food and withholding administering insulin for the first predetermined baseline of time and the action further comprises an indication that insulin can be administered.

5. The method of claim 2, wherein the action further comprises indicating to the user that the first procedure is completed before the first predetermined baseline of time is reached.

6. The method of claim 1, wherein the therapeutic recommendation is a medication dosage or meal based on the estimation of the first parameter.

7. The method claim 1, wherein the analyte is glucose.

8. The method of claim 1, wherein the first procedure is a first set of procedures from the plurality of analyte management procedures, and further comprising recommending the first set of procedures to the user on the display.

9. The method of claim 8, wherein the first set of procedures comprises completed procedures with reasonable level of completeness.

10. The method of claim 1, wherein the analyte is glucose and the first parameter is a carb ratio, an insulin sensitivity factor, a bolus to basal ratio, or a glucose target.

11. The method of claim 1, further comprising displaying to the user on the display an indication of the confidence level score.

12. The method of claim 1, further comprising:
receiving programming input for the plurality of analyte management procedures; and
storing the plurality of analyte management procedures in the memory.

13. The method of claim 1, further comprising transmitting information gathered for the plurality of analyte management procedures to a remote device.

14. The method of claim 13, further comprising receiving programming input for a new plurality of analyte management procedures, wherein the new plurality is based on the information gathered.

15. The method of claim 1, wherein the continuous analyte monitoring device is a continuous glucose monitoring system.

16. The method of claim 1, wherein the actual analyte measurement data is intermittently or periodically received glucose data.

17. The method of claim 1, wherein the plurality of analyte management procedures exists in a plurality of sets, in which successive sets allows for a more detailed and tailored determination of the analyte management parameters.

18. The method of claim 1, wherein displaying to the user the user-instructions associated with the first procedure occurs after receiving the indication from the user to initiate the first procedure.

19. The method of claim 1, wherein the continuous analyte monitoring device comprises the computer, and further comprising:
the continuous analyte monitor receiving programming input for the plurality of analyte management procedures; and
storing the plurality of analyte management procedures in the memory.

20. The method of claim 1, wherein the Kalman Filter is an Extended Kalman Filter.

21. A method for analyte monitoring management including using a computer having a processor for executing instructions, memory operably coupled to the processor comprising the instructions, and a display, the method comprising executing the instructions for:
displaying for user-selection on the display a plurality of analyte management procedures for determining analyte management parameters;
receiving an indication from a user to initiate a first procedure of the plurality of analyte management procedures for determining a first parameter of the analyte management parameters;
displaying to the user user-instructions associated with the first procedure;
receiving from a continuous analyte monitoring device a plurality of actual analyte measurement data of an analyte for the first procedure;
estimating in real-time a plurality of estimated analyte measurement data for the analyte for the first procedure;
analyzing the plurality of actual analyte measurement data and the plurality of estimated analyte measurement data in real-time, and estimating the first parameter using a Kalman Filter;
calculating a first degree of certainty in real-time that the estimation of the first parameter is accurate;
calculating and indicating an estimated time remaining for the first procedure based on an elapsed time since a start of the first procedure and a progression of the first degree of certainty in real-time over the elapsed time;
initiating an action in response to an event, wherein the event is the first degree of certainty in real-time exceeding a predetermined threshold degree of certainty, and wherein the action comprises completing the first procedure and associating a confidence level score to the completed first procedure;
categorizing the level of completeness of the first procedure based on the action, the level of completeness being one of:
a reasonable level of completeness based on the confidence level score being a low confidence level score, or
a best level of completeness based on the confidence level score being above the low confidence level score; and
displaying to the user on the display an indication of the level of completeness.

22. The method of claim 21, wherein the therapeutic recommendation is a medication dosage or meal based on the estimation of the first parameter.

23. The method of claim 21, wherein the analyte is glucose.

24. A method for analyte monitoring management including using a computer having a processor for executing instructions, memory operably coupled to the processor comprising the instructions, and a display, the method comprising executing the instructions for:
displaying for user-selection on the display a plurality of analyte management procedures for determining analyte management parameters;
receiving an indication from a user to initiate a first procedure of the plurality of analyte management procedures for determining a first parameter of the analyte management parameters;
displaying to the user user-instructions associated with the first procedure;

receiving from a continuous analyte monitoring device a plurality of actual analyte measurement data of an analyte for the first procedure;
estimating in real-time a plurality of estimated analyte measurement data for the analyte for the first procedure;
analyzing the plurality of actual analyte measurement data and the plurality of estimated analyte measurement data in real-time;
calculating a first degree of certainty in real-time that the estimation of the first parameter is accurate;
calculating and indicating an estimated time remaining for the first procedure based on an elapsed time since a start of the first procedure and a progression of the first degree of certainty in real-time over the elapsed time;
initiating an action in response to an event, wherein the event is the first degree of certainty in real-time exceeding a predetermined threshold degree of certainty, and wherein the action comprises completing the first procedure and associating a confidence level score to the completed first procedure;
categorizing the level of completeness of the first procedure based on the action, the level of completeness being one of:
a reasonable level of completeness based on the confidence level score being a low confidence level score, or
a best level of completeness based on the confidence level score being above the low confidence level score; and
displaying to the user on the display an indication of the level of completeness.

25. The method of claim 24, wherein the analyte is glucose.

* * * * *